United States Patent [19]
Miettinen-Oinonen et al.

[11] Patent Number: 5,858,767
[45] Date of Patent: Jan. 12, 1999

[54] CELLULASE COMPOSITION FOR BIOFINISHING CELLULOSE-CONTAINING TEXTILE MATERIALS

[75] Inventors: Arja Sisko Kaarina Miettinen-Oinonen, Masala; Minna Johanna Elovainio; Pirkko Liisa Suominen, both of Helsinki, all of Finland

[73] Assignee: Röhm Enzyme Finland Oy, Rajamäki, Finland

[21] Appl. No.: 792,344

[22] Filed: Jan. 31, 1997

[30] Foreign Application Priority Data

Nov. 25, 1996 [FI] Finland ..................................... 964692

[51] Int. Cl.$^6$ ................................................. C12S 11/00
[52] U.S. Cl. ............................................ 435/263; 435/209
[58] Field of Search ...................................... 435/263, 209; 510/320

[56] References Cited

U.S. PATENT DOCUMENTS

| | | | |
|---|---|---|---|
| 3,664,961 | 5/1972 | Norris | 252/99 |
| 4,832,864 | 5/1989 | Olson | 252/174.12 |
| 4,894,338 | 1/1990 | Knowles et al. | 435/172.3 |
| 5,120,463 | 6/1992 | Bjork et al. | 252/174.12 |
| 5,232,851 | 8/1993 | Cox et al. | 435/263 |
| 5,246,853 | 9/1993 | Clarkson et al. | 435/263 |
| 5,290,474 | 3/1994 | Clarkson et al. | 252/174.12 |
| 5,443,750 | 8/1995 | Convents et al. | 252/174.12 |
| 5,525,507 | 6/1996 | Clarkson et al. | 435/263 |
| 5,650,322 | 7/1997 | Clarkson et al. | 435/263 |

FOREIGN PATENT DOCUMENTS

| | | |
|---|---|---|
| WO 92/06165 | 4/1992 | WIPO . |
| WO 92/06209 | 4/1992 | WIPO . |
| WO 92/06210 | 4/1992 | WIPO . |
| WO 92/06221 | 4/1992 | WIPO . |
| WO 92/17572 | 10/1992 | WIPO . |
| WO 92/17574 | 10/1992 | WIPO . |
| WO 93/22428 | 11/1993 | WIPO . |
| WO 94/07983 | 4/1994 | WIPO . |
| WO 94/23113 | 10/1994 | WIPO . |
| WO 95/16782 | 6/1995 | WIPO . |
| WO 95/25840 | 9/1995 | WIPO . |
| WO 96/17994 | 6/1996 | WIPO . |
| WO 96/29397 | 9/1996 | WIPO . |
| WO 96/34945 | 11/1996 | WIPO . |

OTHER PUBLICATIONS

Bailey, M.J. and Nevalainen, K.M.H., "Introduction, isolation and testing of stable *Trichoderma reesei* mutants with improved production of solubilizing cellulase," *Enz. Micr. Tech.* 3(2):153–157 (1981).

Bhat, K.M. et al., "The endo–(1→4)–β–D–glucanase system of *Penicillium pinophilum* cellulase: isolation, purification, and characterization of five major endoglucanase components," *Carbohydrate Research* 190:279–297 (1989).

Bhikhabhai, R. et al., "Isolation of Cellulolytic Enzymes from *Trichoderma reesei* QM 9414," *J. Applied Biochem.* 6:336–345 (1984).

Bühler, R., "Double–Antibody Sandwich Enzyme–Linked Immunosorbent Assay for Quantitation of Endoglucanase I of *Trichoderma reesi*," *Appl. Environ. Microbiol.* 57(11):3317–3321 (1991).

Ghose, T.K., "Measurement of Cellulase Activities," Commission on Biotechnology, International Union of Pure and Applied Chemistry (1984).

Karkunen, T. et al., "High frequency one–step gene replacement in *Trichoderma reesi*. I. Endoglucanase I overproduction," *Mol. Gen. Genet.* 241:515–522 (1993).

Mach, R.L. et al.. "Transformation of *Trichoderma reesi* based on hygromycin B resistance using homologous expression signals," *Curr. Genet.* 25:567–570 (1994).

Mattern, I. E. et al., "Transformation of *Aspergillus oryzae*," in Abstracts of the 19th Lanteren Lectures on Molecular Genetics of Yeasts and Filamentous Fungi and its Impact on Biotechnology, Lanteren, the Netherlands, 1987, p. 34.

Nevalainen, H., "Genetic improvement of enzyme production in industrially important fungal strains," VTT, Technical Research Centre of Finland, publication 26, Espoo, Finland (1985), pp. 3–58.

Penttilä, M. et al., "Homology between cellulase genes of *Trichoderma reesi*: complete nucleotide sequence of the endoglucanase I gene," *Gene* 45:253–263 (1986).

Penttilä, M. et al., "A versatile transformation system for the cellulolytic filamentous fungus *Trichoderma reesei*," *Gene* 61:155–164 (1987).

Saloheimo, M. et al., "EGIII, a new endoglucanase from *Trichoderma reesei*: the characterization of both of gene and enzyme," *Gene* 63:11–21 (1988).

Schülein, M., "Cellulase of *Trichoderma reesei*," *Methods Enzymol.* 160:234–242 (1988).

Shoemaker, S. et al., "Molecular cloning of exo–cellobiohydrolase I derived from *Trichoderma reesei* strain L27," *Bio/Technology* 1:691–696 (1983).

Suominen, P. et al., "High frequency one–step gene replacement in *Trichoderma reesei*. II Effects of deletions of individual cellulase genes," *Mol. Gen. Genet.* 241:523–530 (1993).

Teeri, T. et al., "Homologous domains in *Trichoderma reesei* cellulolytic enzymes: gene sequence and expression of cellobiohydrolase II," *Gene* 51:43–52 (1987).

(List continued on next page.)

*Primary Examiner*—Charles L. Patterson, Jr.
*Attorney, Agent, or Firm*—Sterne, Kessler, Goldstein & Fox P.L.L.C.

[57] ABSTRACT

The present invention is directed to a new cellulase composition for finishing of cellulose-containing textiles, especially cotton. The improved properties of the cellulase composition are based on an elevated content of CBHII cellobiohydrolase type component in an otherwise normal background cellulase composition. When the composition with elevated CBHII contents is used improved color properties, increased lightness, improved visual appearance and reduced pilling tendencies are achieved. The strength properties of the textile materials are essentially unchanged as compared to previously used cellulase compositions.

25 Claims, 2 Drawing Sheets

OTHER PUBLICATIONS

Teeri, T. et al., "The molecular cloning of the major cellulase gene from *Trichoderma reesei*." Bio/Technology I:696–699 (1983).

Teeri, T., "The cellulolytic enzyme system of *Trichoderma reesei*: Molecular cloning, characterization and expression of the cellobiohydrolase genes," Technical Reserch Centre of Finland, Valtion Teknillinen Tutkimuskesku, Espoo 1987, p. 18.

van Tilbeurgh, H. et al., "Fluorogenic and chromogenic glycosides as substrates and ligands of carbohydrases," *Methods Enzymol.* 160:45–59 (1988).

Wood, T.M. et al., "Aerobic and anaerobic fungal cellulases, with special reference to their mode of attack on crystalline cellulose," *FEMS Symposium No. 43: Biochemistry and Genetics of Cellulose Degradation*, pp. 31–52 (1988).

Aho, S. et al., "Monoclonal antibodies against core and cellulose–binding doamins of *Trichoderma reesei* cellobiohydrolases I and II and endoglucanase I," *Eur. J. Biochem.* 200(3):643–649 (1991).

Harkki, A. et al., "Genetic engineering of *Trichoderma* to produce strains with novel cellulase profiles," *Enzyme Microb. Technol.* 13(3):227–233 (1991).

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear     ( i i ) MOLECULE TYPE: nucleic acid     ( x i ) SEQUENCE DESCRIPTION: SEQ ID NO:1:

CCGCGGACTG GCATC 15

( 2 ) INFORMATION FOR SEQ ID NO:2:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear     ( i i ) MOLECULE TYPE: nucleic acid     ( x i ) SEQUENCE DESCRIPTION: SEQ ID NO:2:

CCGCGGACTG CGCATC 16

CELLULASE COMPOSITION FOR BIOFINISHING CELLULOSE-CONTAINING TEXTILE MATERIALS

THE BACKGROUND OF THE INVENTION

1. The Technical Field of the Invention

The present invention is directed to a cellulase composition having an elevated content of CBHII type cellulase. Said cellulase composition is obtainable from bacteria or fungi, especially from Trichoderma. The invention is also related to treatment media containing said cellulose composition as well as to methods for treating and finishing textile materials.

2. The State of the Art

Cellulase treatment of cellulose-containing textile materials during their manufacture or finishing is known per se in the art. The enzymatic treatment for finishing of cellulose-containing textile materials is called biofinishing. Biofinishing has been used to remove all kinds of impurities and individual loose fibre ends that protrude from the textile surface. The key benefits offered by biofinishing with cellulases are permanent improval of depilling, cleared surface structure by reduced fuzz, improved textile handle, such as softness, smoothness and a silkier feel, improved drapability and brighter colors of the textile and improved moisture absorbability.

Significant strength loss of the fabric as a result of cellulase treatment is a problem associated with cellulase treatment. The strength loss is caused by cellulase-induced hydrolysis of beta-1,4-glucosidic bonds of cellulose, which in turn results in partial degradation of cellulosic polymer, and further, can result in strength loss of the fabric.

In the treatment of fabrics, cellulase derived from fungi, for example from *Trichoderma reesei*, is generally employed, such cellulase being composed of cellobiohydrolase (CBH), endoglucanase (EG) and beta-glucosidase (BG) type components. The CBH and EG components can further be divided into CBHI and CBHII types and into several various EG types, the main types of the latter being EGI and EGII. The BG components do not react with cellulosic polymers, but further cleave the degradation products, for example cellobiose, that are formed as a result of the synergistic effect of the CBH and EG components.

A method for treating cotton fabrics, prior to dyeing and finishing, with cellulase solution in order to remove lint and loose surface fibres to impart a better appearance to the fabric is disclosed in the U.S. Pat. No. 5,232,85. The employed cellulase can be produced, for example, by *Trichoderma reesei, T. koningii, Penicillium sp* or *Humicola insolens* species. In the given examples, CYTOLASE 123-cellulase (Genencor Int.) was used with no detailed composition given in said publication. In addition to cellulase, the cellulase solution may contain buffers, surfactants, abrasion agents, and the like. After treatment, the tensile strength of the cotton woven fabric was reported to be at least 50 percent of the tensile strength of untreated fabric.

The original natural cellulase composition obtainable from the fermentation medium, which is derived directly from the microbes, for example from *T. reesei* fungi, is seldom suitable as such to give a desired result. The original cellulase composition may comprise about 45–80% CBHI, 10–25% CBHII, 5–15% EGI and 8–15% EGII of the total cellulase protein content. The interrelations of the CBH and EG components contained in a composition may hence be changed by various methods known to persons skilled in the art. Such methods include, for example, fractionation and genetic engineering.

The U.S. Pat. No. 5,120,463 for example discloses a detergent composition comprising a surfactant and additionally 0.002 to 10 weight percent of cellulase composed of CBHI type and EG type components with the ratio of CBHI to (EGI+EGII) being $\geq 10:1$.

The International Patent Application WO 93/22428 discloses a method for treating cotton fabrics with fungal cellulase compositions comprising CBHI type and EG type components in a weight ratio greater than 10:1. The application mentions that the tensile strength of treated fabric is at least about 50 percent of the tensile strength of untreated fabric. No test results, however, are given.

In the International Patent Publication WO 94/23113 a method for treating cotton-containing and non-cotton cellulosic fabrics during manufacture to reduce lint generation is also described. The cellulase compositions contains all EG type components to all CBH type components in a ratio of greater than 5:1.

In the International Patent Publication WO 92/06221 cotton-containing fabrics treated with a cellulase solution essentially free from CBHI type cellulase components are said to have a decreased strength loss as compared to fabrics treated with cellulase solution containing a complete cellulase composition.

It is also known in the art that the activity of the cellulase composition depends on the acidity of the environment in which the treatment is carried out. Most generally, the activity is at its highest at slightly acid pHs, even though compositions functioning in a neutral environment may also be employed, and even such cellulase compositions are known to act in alkaline conditions. However, compositions used in a neutral or alkaline environment have a prolonged reaction time, i.e. the compositions are acting slower. Because time means money, time consuming treatments are not only less time-effective but also less cost-effective. Alternatively, more equipment is required to treat the same amount of fabrics in the same time. This is also expensive and requires additional space and facilities. Naturally, buffers known to persons skilled in the art are used to adjust the acidity of cellulase treatment media, but it does not solve all the problems.

The problem of obtaining improved color retention/restoration properties as well as improved softening and feel and visual appearance properties to cotton fabrics has been discussed in several patents and patent applications.

In the U.S. Pat. No. 5,090,474 for example a detergent composition containing substantially pure EGIII is described. The composition contains no more than 5 weight percent of CBHI type components.

The International Patent Publication WO 92/06210 describes a cellulase composition, which is enriched with unspecified endoglucanase type components. The ratio of EG type components to all CBHI type components is greater than 5:1. The composition is said to impart improved softening properties as well as retention/restoration properties to the detergent composition when used in acidic, neutral or alkaline washing media.

U.S. Pat. No. 5,246,853 discloses an improved method for treating cotton-containing fabrics with fungal cellulase compositions which are essentially free from CBH I type cellulase components, but contains at least 10% of unspecified EG type components based on the total weight of proteins in the cellulase solution.

In the International Patent Publication WO 92/06165 a cellulase composition is disclosed which composition contains 0.01–5 weight percent cellulase components. The compositions contains one or more unspecified EG type components and of all cellulase components less than 5 weight percent is of CBH I type components.

The International Patent Publication WO 95/25840 describes a cellulase composition, which is essentially free from CBH I type cellulase components and has a weight ratio of all EG-type components to all CBH I type components of greater than 5:1. Said International Patent Application corresponds to U.S. Pat. No. 5,525,507, which discloses a composition useful for treating non-cotton material. The composition is essentially free of all CBHI type cellulase components and the improved properties are achieved by modifying the naturally complete fungal cellulase composition by adding at least 10 percent of unspecified endo-glucanase components.

The International Patent Publication WO 92/17572 describes a cellulase composition, which is essentially free from CBH I type cellulase components and comprises at least about 20 weight percent of unspecified EG type components.

The International Patent Publication WO 92/17574 describes a cellulase composition, which comprises one or more unspecified EG component and one more CBHI component and the ratio of all EG to all CBHI components is greater than 5:1.

In view of the above, the primary problem of using cellulase compositions in the treatment and finishing of cellulose-containing textile materials has not only been the strength loss of the fabric as a result of the cellulase treatment but also the fact that even if the proportions of CBH and EG type components have been changed in the most subtle ways as suggested in the prior art patents and patent applications no significant change in the biofinishing properties has been achieved. It seems as if the different ratios of CBH and EG type components are varied more or less randomly and the results, such as removal of impurities and individual loose fibre ends that protrude from the textile surface are as randomly obtainable. The key benefits claimed by the patents and patent application using different ratios of EG and CBH type components in biofinishing, i.e. permanent improval of depilling, cleared surface structure by reduced fuzz, improved textile handle, such as softness, smoothness and a silkier feel, improved drapability and brighter colors of the textile and improved capability of absorbing moisture seems to be essentially unchanged even if the ratios of EG and CBH vary.

Furthermore, the removal of certain components and addition of other components to the natural complete fungal cellulase composition is not necessarily sufficiently cost-effective.

We have now surprisingly found that it is not the different ratios of CBH components others than CBHII and EG components that gives the improved properties in manufacturing and finishing of textiles, but an increased level of CBHII is responsible for the improvement. The same or even better results in manufacturing and finishing are obtained as soon as even small amounts of CBHII type component(s) are added to the natural complete cellulase composition background. This improvement is totally independent of the ratios of CBH and EG disclosed in prior art.

Thus, the objective of the present invention is to provide an improved cellulase composition for treating cellulose-containing textile materials that gives a smooth feel, improved appearance and softness and improved depilling properties to the textile.

In particular, the objective of the present invention is to provide an improved cellulase composition for treating cellulose-containing textile materials that would not result in significant strength loss of the textile as a result of the treatment.

Further, the objective of the present invention is to provide an improved treatment medium for cellulose-containing textile materials that may comprise, in addition to the cellulase composition of this invention, for example, surfactants, polymers, buffers, bulk agents, preservatives, stabilizers and/or abrasion agents.

The objective of the present invention is to provide compositions with a decreased reaction time, i.e. compositions which act more rapidly. This means more time- and cost-effective treatment procedures and savings in equipment as well as treatment facilities.

The objective of the present invention is additionally to provide an improved method for treating cellulose-containing textile materials so as to preserve the strength properties, as well as to obtain an improved appearance and smooth feel of the textile.

The described objectives of the present invention have been achieved by employing a cellulase composition invention which comprises elevated amounts of CBHII type cellulase as compared to the natural complete cellulase compositions as well as those cellulase compositions known from prior art.

The improved cellulase composition of the present invention is obtainable from a cellulase solution produced by cultivating fungi or bacteria and collecting the spent essentially cell-free fermentation broth or medium containing the naturally occurring complete background cellulase components such as CBH and EG components, but above all an elevated content of CBHII components as compared to the natural complete cellulase compositions and the prior art cellulase compositions with different CBH and EG ratios. The elevated content of CBHII should be such that the desired effects are achieved. The CBHII type cellulase being the component which is essential for obtaining the objectives and benefits of the present invention.

THE SUMMARY OF THE INVENTION

The present invention is related to an improved cellulase composition for treating cellulose-containing textile materials during their manufacture or for their finishing. The improved cellulase composition comprises a desired somewhat elevated content of CBHII type components as compared to the natural complete cellulase composition obtainable from a cell-free fermentation media. When such cellulase compositions with an elevated content of CBHII are used for treating cellulose containing fabrics the results are improved biofinishing effects and essentially no strength loss in the textile materials as compared with the results obtainable with prior art ratio modified or natural complete cellulase compositions.

The improved cellulase composition of the present invention comprises an elevated content of the CBHII type component as compared to previously used complete and modified cellulase compositions. The amount of CBHII being at least 20–100 weight percent, preferably at least 25–60 weight percent, most preferably at least 30–40 weight percent of the total cellulase (protein) content.

The improved cellulase composition of the present invention can also be essentially free from substantially all CBH type components except CBHII and/or from substantially all EG type components.

The improved cellulase composition of the present invention is obtainable from fungi or bacteria, especially from fungi such as Trichoderma, Penicillium, Aspergillus, Humicola or Fusarium genera. The most preferred source of the cellulase composition being a *Trichoderma reesei* species, especially CBHII overproducing *Trichoderma reesei* strains.

The present invention also provides an improved treatment medium (composition) for treating cellulose-containing textile materials. Said treatment medium also contains the improved cellulase composition with the increased amount of CBHII type cellulase as compared to prior art modified noncomplete and natural complete cellulase compositions. The cellulase containing treatment medium not only gives improved properties during manufacturing and finishing to the cellulose-containing textile materials but also causes the same or less strength loss when compared with cellulose-containing materials treated under the same conditions with cellulase compositions without the elevated CBHII content.

The treatment medium is useful for biofinishing of cellulose-containing textile materials. Said medium contains surfactants, polymers, buffers, bulking agents, preservatives, stabilizers and/or abrasion agents.

The present invention is also related to a method for treating cellulose-containing textile materials, wherein the medium defined above is used for treating or finishing of cellulose-containing textile materials. Said modifiable cellulose-containing textile materials are cotton, flax, ramie, jute, viscose, MODAL, lyocell, cupro, etc, especially cotton.

THE DETAILED DESCRIPTION OF THE INVENTION

Definitions

In the description that follows, a number of terms used in textile industry and enzyme technology as well as recombinant DNA technology are extensively utilized. In order to provide a clear and consistent understanding of the specification and claims, including the scope to be given such terms, the following definitions are provided.

Cellulose-containing textile materials or fabrics. The term "cellulose-containing textile materials or fabrics" as used in the present invention refers to textile material composed solely or partly of cellulosic fibres. The textile material includes fibre, yarn, woven fabric, knit, or a ready-made garment, in whose manufacture cotton, flax, linen, hemp, ramie, jute or man-made cellulosic fibres, for example, viscose, Polynosic Modal, lyocell (e.g. Tencel$^R$), Cupro, etc., have been used as raw material. When using synthetic man-made fibres, the amount of cellulosic fibre in the textile material has to be at least 30 percent, preferably over 50 percent.

Complete cellulase composition. The term "complete cellulase composition" as used herein refers to cellulases derived from fungi, for example from *Trichoderma reesei*. Such cellulase being composed of cellobiohydrolase (CBH), endoglucanase (EG) and beta-glucosidase (BG) type components. The CBH and EG components can further be divided into CBHI and CBHII types and into several various EG types, the main types of the latter being EGI and EGII. The BG components do not react with cellulosic polymers, but further cleave the degradation products, for example cellobiose, that are formed as a result of the synergistic effect of the CBH and EG components.

The original cellulase composition obtainable from the fermentation medium, which is derived directly from the microbes, for example from *T. reesei* fungi having a cellulase composition comprising about 45–80% CBHI, 10–25% CBHII, 5–15% EGI and 8–15% EGII of the total cellulase protein content is considered to be the complete cellulase composition according to the present invention. The ratio of EG:CBH in *T. reesei* ALKO3798 the CBHII overproducing strain is estimated to be approximately 0.1–0.4:1 and the ratio of EG:CBHI is approximately CBHI:EG 0.2–0.6:1 and the ratio between CBHI:EG is approximately 2–4:1 and the ratio between CBH:EG is estimated to be approximately 3–6:1.

Modified cellulase composition. The term "modified cellulase composition" as used herein refers to the complete cellulase composition in which the interrelations of the CBH and EG components contained in a composition have been changed by various methods known to persons skilled in the art. Such methods include, for example, fractionation and genetic engineering as well as combining different cellulase solutions.

Essentially free from CBH-type components means that at least one CBH-type component except CBHII is missing from the cellulase composition, i.e. said composition is produced by a host from which the genes encoding said proteins are removed.

Essentially free from EG-type components means that at least one EG-type component is missing from the cellulase composition. The EG-type components can be EGI, EGII, EGIII, EGV etc. or all or any combination of said EG-proteins. Said composition are obtainable by cultivating host from which one or more genes encoding said proteins are removed.

Biofinishing. "Biofinishing" refers to the use of enzymes in a controlled hydrolysis of cellulosic fibers in order to modify the fabric or yarn surface in a manner that prevents permanently pilling, improves fabric handle like softness and smoothness, clears the surface structure by reducing fuzzing, which results in clarification of colors, improves the drapability of the fabric, improves moisture absorbability and which may improve also the dyeability.

Detergent. By detergent is meant a cleansing agent that can contain surface active agents (anionic, non-ionic, cationic and ampholytic surfactants), builders and other optional ingredients such as antiredeposition and soil suspension agents, optical brighteners, bleaching agents, dyes and pigments and hydrolases. Suitable listing of the contents of detergents is given in U.S. Pat. No. 5,433,750, a suitable list of surfactants is given in U.S. Pat. No. 3,664,961.

Enzyme preparation. By "enzyme preparation" is meant a composition containing enzymes. Preferably, the enzymes have been extracted from (either partially or completely purified from) a microbe or the medium used to grow such microbe.

"Extracted from" means that the desired enzymes are separated from the cellular mass. This can be performed by any method that achieves this goal, including breaking cells and also simply removing the culture medium from spent cells. Therefore, the term "enzyme preparation" includes compositions containing medium previously used to culture a desired microbe(s) and any enzymes that have been released from the microbial cells into such medium during the culture or downstream processing steps.

By a host that is "substantially incapable" of synthesizing one or more enzymes is meant a host in which the activity of one or more of the listed enzymes is depressed, deficient, or absent when compared to the wild-type.

By an amino acid sequence that is an "equivalent" of a specific amino acid sequence is meant an amino acid sequence that is not identical to the specific amino acid sequence, but rather contains at least some amino acid changes (deletions, substitutions, inversions, insertions, etc) that do not essentially affect the biological activity of the protein as compared to a similar activity of the specific amino acid sequence, when used-for a desired purpose. The biological activity of a cellulase, is its catalytic activity, and/or its ability to bind to cellulosic material. Preferably, an "equivalent" amino acid sequence contains at least 80%–99% identity at the amino acid level to the specific amino acid sequence, most preferably at least 90% and in an especially highly preferable embodiment, at least 95% identify, at the amino acid level.

Cloning vehicle. A cloning vehicle is a plasmid or phage DNA or other DNA sequence (such as a linear DNA) that provides an appropriate nucleic acid carrier environment for the transfer of a gene of interest into a host cell. The cloning vehicles of the invention may be designed to replicate autonomously in prokaryotic and eukaryotic hosts. In fungal hosts such as Trichoderma, the cloning vehicles generally do not autonomously replicate and instead, merely provide a vehicle for the transport of the gene of interest into the Trichoderma host for subsequent insertion into the Trichoderma genome. The cloning vehicle may be further characterized by one or a small number of endonuclease recognition sites at which such DNA sequences may be cut in a determinable fashion without loss of an essential biological function of the vehicle, and into which DNA may be spliced in order to bring about replication and cloning of such DNA. The cloning vehicle may further contain a marker suitable for use in the identification of cells transformed with the cloning vehicle. Markers, for example, are antibiotic resistance. Alternatively, such markers may be provided on a cloning vehicle which is separate from that supplying the gene of interest. The word "vector" is sometimes used for "cloning vehicle."

Expression vehicle. An expression vehicle is a cloning vehicle or vector similar to a cloning vehicle but which is capable of expressing a gene of interest, after transformation into a desired host. When a fungal host is used, the gene of interest is preferably provided to a fungal host as part of a cloning or expression-vehicle that integrates into the fungal chromosome, or allows the gene of interest to integrate into the host chromosome. Sequences that are part of the cloning vehicle or expression vehicle may also be integrated with the gene of interest during the integration process. In *T. reesei*, sites of integration to which the gene of interest can be directed include the cbh and/or the egl loci. Most preferably, the gene of interest is directed to replace one or more genes encoding undesirable characteristics.

The gene of interest is also preferably placed under the control of (i.e., operably linked to) certain control sequences such as promoter sequences provided by the vector (which integrate with the gene of interest). Alternatively, the control sequences can be those at the insertion site.

The expression control sequences of an expression vector will vary depending on whether the vector is designed to express a certain gene in a prokaryotic or in a eukaryotic host (for example, a shuttle vector may provide a gene for selection in bacterial hosts). Expression control sequences can contain transcriptional regulatory elements such as, promoters, enhancer elements, and transcriptional termination sequences, and/or translational regulatory elements, such as, for example, translational initiation and termination sites.

THE GENERAL DESCRIPTION OF THE INVENTION

In the manufacturing or finishing of cellulose-containing materials, it was unexpectedly found that by using a cellulase composition, which comprised an increased amount of CBHII type cellulase component in an otherwise natural complete cellulase composition, a cellulose-containing textile product with essentially the same or improved properties could be produced. The cotton containing textile material also had an improved nice appearance and feel, and showed a reduced tendency of pilling, and additionally maintained its strength.

In order to obtain the improved results of the present invention during manufacturing and finishing the cellulase composition or treatment media containing compositions, should have more or less elevated CBHII contents.

It has been shown that using the cellulase composition of the present invention improved appearance, softness, drapability, absorption of moisture, and brighter colors of cellulose-containing textile materials is achieved. Also a reduced tendency of pilling and fuzzing as well as richer colors are obtained.

Fungi and bacteria can be used as source material for producing the cellulase composition of the present invention. Preferably the cellulase compositions of this invention are derived from fungi, for example from species of Trichoderma, Aspergillus, Penicillium, Humicola or Fusarium genera. *Trichoderma reesei* being the fungi of preference for producing the cellulase composition. According to prior art the natural complete cellulase compositions comprising CBH components and various EG components, are not as such applicable to the treatment of cellulose-containing textile materials for producing the desired end result. The suggested methods of producing compositions which are modified to give different ratios between the CBH and EG are neither necessary to achieve the desired results. An elevated CBHII-content in the complete cellulase background composition is the only thing required to obtain the desired results.

When some other strain than Trichoderma is used for obtaining the cellulase composition, it is possible, in a similar fashion, to modify the ratios of the types of cellulase produced by the employed strain, which produces cellulases functionally corresponding to those produced by Trichoderma and adding a suitable amount of CBHII, which gives the desired result.

For a desired and good end result, it is essential that the cellulase composition contains a more or less significantly increased amount of CBHII type endoglucanases of Trichoderma. If the cellulase composition is derived from Trichoderma, the cellulase composition of the present invention comprises in addition to the elevated CBHII-content, EGI and EGII components and possibly minor amounts of other EG components, such as EGIII and EGV as well as the CBHI component, but said more or less undesired EG and CBH components, the ratio of which is of no major importance, can also be removed using conventional recombinant and fractionation techniques.

The increased CEHII content can be provided in cellulase compositions with a relative ratio of CBHI or EGI to other components increased or decreased by methods known per se in the art, but as discussed above it is no prerequisite for obtaining the desired results. In the cellulase composition of the present invention, however, the ratios of the weights of CBH and EG components are not crucial. It is more important that the amount of CBHII type components in the composition is more or less significantly elevated over the normal complete level of obtainable cellulase compositions. This means that the proportion of CBHII should be at least 20–100 weight percent of the total weight of the natural complete composition of cellulase proteins. More preferably, the amount of CBHII should be at least 25–60 weight percent, and most preferably at least 30–40 weight percent of the cellulase composition. Naturally, the cellulase composition can comprise almost 100 weight percent of CBHII of the total cellulase content, but this is in no way the preferred embodiment and not necessarily required for obtaining the desired results. The preferred mode of the present invention is a natural complete background cellulase composition with elevated CBHII-content.

Enzyme activity is one concept applied in determining the properties of enzymes. The enzyme activities used in the present patent application are ECU, FPU and MUL, which are defined as follows:

ECU

The endo-1,4-beta-glucanase in the sample hydrolyses the hydroxyethylcellulose substrate, and the resulting reducing sugars are assayed spectrophotometrically using a dinitrosalicylic acid reagent (DNS). One unit of endo-1,4-beta-glucanase is defined as the amount of enzyme-producing one nmole of reducing sugars as glucose in one second (1 ECU=1 nkat), (Bailey, M. and Nevalainen, H., 1981).

FPU

The cellulase in the sample hydrolyses the filter paper used as a substrate, and the resulting reducing sugars are assayed spectrophotometrically using a DNS reagent. The filter paper degrading activity is described as FPU units. The calculation is based on the definition of the International Unit (IU). 1 IU=1 micromol min.$^{-1}$ of product formed (reducing sugars as glucose) (IUPAC, 1984).

MUL

The cellobiohydrolase (CBHI) and endoglucanase (EGI) of the sample hydrolyse the 4-methylumbelliferyl-beta-D-lactoside that acts as a substrate, whereby methylumbelliferone is released that can be measured spectrophotometrically. The method can be applied in the determination of cellobiohydrolase I (CBHI) activity. The method also measures the endoglucanase I (EGI) activity, whose proportion can be determined by inhibiting the activity of cellobiohydrolase using 5 mM of cellobiose. One MUL unit is the amount of enzyme activity that in one second under the determination conditions, releases 1 nmol of methylumbelliferone from 4-methylumbelliferyl-beta-D-lactoside (van Tilbeurgh et al., 1988).

Treatment of cellulose-containing textile materials with the cellulase composition of the present invention imparts a smooth feel, softness and good appearance as well as good depilling to the textiles. The treated cotton-containing fibres treated with the composition of this invention have kept their structure as well as or better than cellulase compositions comprising prior or conventional cellulase compositions.

It has also been possible to show that the strength properties of cellulose-containing textile materials, i.e. bursting strength, breaking strength and tearing strength have remained better in textile materials treated with the compositions of this invention than the corresponding properties in cellulose-containing textile materials treated with cellulase compositions lacking the elevated CBHII-content.

Treatment media of cellulose-containing textile materials with compositions disclosed in the present invention may contain, in addition to enzymes, e.g. surfactants, polymers as for example PVA and PVP polymers, buffers as for example citrates, acetates and phosphates for regulating the acidity of the solutions, possibly bulk agents, conventional preserving agents, stabilizers and abrasion agents.

The dosage of cellulase products in a solution depends on the desired result, application, the activity of the cellulase product etc. Suitable cellulase dosages as disclosed in the present invention, correspond to the dosages of typical commercial liquid cellulases, as for example Ecostone L, Ecostone L 20, Biotouch L (Primalco Ltd, Biotec, Nurmijarvi, Finland). The suitable dosages thus fall within the range of 0.05 to 15 percent, more preferably within 0.5 to 6 percent of the weight of the textile material being treated.

The suitable enzyme dosages for imparting biofinishing treatment to textile materials depend on the desired result, on the treatment method and the activity of the enzyme product. The dosages are about 0.05 to 10 percent, more preferably about 0.5 to 5 percent of the weight of the treated textile material, these dosages corresponding to the dosages of typical commercial liquid cellulases, as for example Biotouch L, Biotouch C 601, Ecostone L 20 or Ecostone C 80 (Primalco Ltd, Biotec, Nurmijärvi, Finland).

The pH range for applying the cellulase composition of this invention is dependent on the pH activity profile of the enzyme. When enzymes functioning at acid pHs are being employed, the pH of the application environment is preferably within the range of 3.5 to 7, more preferably within the range of 4 to 5.5.

The cellulase composition of the present invention, which contains considerable amounts of Trichoderma CBHII type endoglucanases, can be produced by e.g. fractionation or mutation of the used production strain, or by genetic engineering. A cellulase composition with elevated amounts of CBHII type endoglucanases can be prepared correspondingly. The most convenient way of producing a product with increased amount of CBHII protein is to add copies of the gene encoding the CBHII protein to the production strain, e.g. from the Trichoderma strain, as described in Example 1. The selected Trichoderma strain or other employed production organism can be a wild type strain, or a strain more suitable for use as a production organism developed from the wild type strain by further mutation or genetic engineering. As for *Trichoderma reesei*, suitable strains include, for example, the wild type strain *T. reesei* QM6a and the derived mutant strains, e.g. QM9414 and RutC-30, developed for cellulase production, and strains further developed from these, in which e.g. the cellulase and/or hemicellulase level has been further raised, and/or in which the level of produced protease has been lowered. VTT-D-79125 and ALKO2221 (a mutant strain with a low level of protease production) and their derivatives, as for example the strain overproducing the CBHII enzyme, whose construction is disclosed in Example 1, are examples of strains that have been further developed. In said strains one or more gene coding for CBH or EGs others than CBHII can be replaced with a gene encoding CBHII.

A general description of the methods for inserting the gene encoding the CBHII protein, and of the method for increasing the production level of the CBHII protein in *Trichoderma reesei* is described in the following. Applying the same method, it is possible to change the ratios of cellulases also in other species and, for example, to adding copies of genes encoding Trichoderma CBHII type cellulase (s) or to replace some native genes with genes encoding Trichoderma CBHII type cellulase(s).

The gene encoding the CBHII protein (cbh2; Teeri et al., 1987); can be inserted into the selected Trichoderma strain together with a marker gene, or, for example, replace a gene encoding EGI (egl1; Penttila et al., 1986), or another gene encoding a not required protein. When the cbh2 gene replaces, e.g. the egl1 gene, the CBHII activity of the enzyme mixture produced by the strain is higher than in the enzyme mixture produced by strains from which the cbh2 gene is deleted or exist only in one copy. It is also possible to insert additional copies without deleting anything. Any marker suitable for Trichoderma can be employed as a marker gene, as for example amdS (e.g. from plasmid p3SR2; Kelly and Hynes, 1985), hygB (e.g. from plasmid pRLM$_{ex}$30; Mach et al., 1994) and ble (e.g. from plasmid pAN8-1, Mattern and Punt, 1988). For auxotrophic strains, the complementary gene for the auxotrophy concerned can also be employed as a marker.

The selected marker gene and the cbh2 gene, are ligated between the 5' and 3' flanking regions of the target gene forming a targeting plasmid. Using the flanking regions, homologous recombination can occur and the desired genes can be targeted to give place for an inserted cbh2 gene. The principle of gene replacement is described by Suominen et al. (1993). For the targeting frequency to be satisfactorily high, the flanking regions must be long enough, e.g. in Trichoderma at least 1.5 kb in length; examples of flanking regions suitable for replacing cellulase genes have been described by Suominen et al. (1993).

Strains of CBHII-overproducing phenotypes can be selected from among transformants, for example, by analysing the amount of secreted CBHII protein with ELISA method (Buehler, 1991) from the culture media.

The production level of the CBHII protein can be raised in a selected strain, for example in the Trichoderma reesei strain (examples of applicable T. reesei strains have been given in the foregoing) by mutation or by increasing the copy number of the cbh2 gene, as is described in Example 1E. In addition to the cbh1 promoter, also other promoters, suitable for the selected strain, can be used for the expression of the cbh2 gene. Any marker suitable for Trichoderma may be used as a marker gene in the transformation, as has been described in the foregoing.

The sources referred to in the above description are given in the reference list in the end of the specification.

The following examples and figures provide further details of the preparation of the cellulase composition of the present invention, and the effect of the cellulase composition on the properties of cellulose-containing textile materials.

EXAMPLE 1

Construction of the strains

Figure 1:
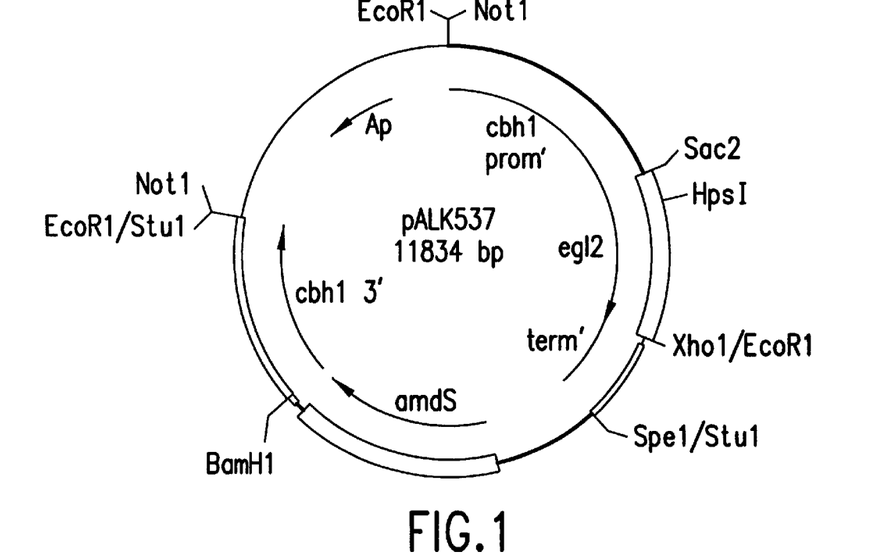
FIG. 1 shows the plasmid map of pALK537.

Trichoderma reesei strains overproducing each of the main Trichoderma cellulase, endoglucanases I and II (EGI and EGII) and cellobiohydrolases I and II (CBHI and II), were constructed for the production of different cellulase preparations.
A. Construction of EGII overproducing Trichoderma reesei strain In construction of the Trichoderma reesei EGII overproducing strain, the parental T. reesei strain VTT-D-79125 was transformed with the expression cassette from the plasmid pALK537 (FIG. 1). In the cassette EGII is expressed from the strong cbh1 promoter. T. reesei VTT-D-79125 is a hypercellulolytic mutant strain that contains all the main Trichoderma cellulases (Nevalainen, 1985).

The plasmid pALK537 contains:

T. reesei cbh1 (cellobiohydrolase 1) promoter is from Trichoderma reesei VTT-D-80133 (Teeri et al., 1983). The 2.2 kb EcoRI-SacII fragment was used in the construct. The sequence of the promoter area preceeding the ATG was published by Shoemaker et al. (1983). The last 15 nucleotides of the T. reesei L27 cbh1 promoter (the SacII site is underlined) are CCGCGGACTGGCATCS (SEQ ID NO:1), (shoemaker et al., 1983). The cbh1 promoter from T. reesei strain VTT-D 80133 has been sequenced in the laboratory of Primalco Ltd. and one nucleotide difference in the DNA sequence has been noticed within the above mentioned region. In the T. reesei VTT-D-80133 the sequence preceeding the ATG is CCGCGGACTGCGCATG (SEQ ID NO. 2).

The nucleotides missing from the promoter (10 bps after the SacII to the ATG) were added and the exact promoter fusion to the signal sequence of egl2 (endoglucanase 2) cDNA was done by using the PCR (polymerase chain reaction) method. The fusion and the PCR fragment were sequenced to ensure that no errors had occurred in the reaction.

T. reesei egl2 (endoglucanase 2, originally called egl3) cDNA. The nucleotide sequence of the egl2 cDNA is described in Saloheimo et al. (1988). In the plasmid pALK537 a 1.4 kb fragment (from the signal sequence to EcoRI site) was used.

T. reesei cbh1 terminator from T. reesei VTT-D-80133 (Teeri et al., 1983). The 739 bp AvaII fragment starting 113 bp before th STOP codon of the cbh1 gene was added after the egl2 cDNA.

cbh1 3'-fragment: The 1.4 kb BamHI-EcoRI fragment was isolated from T. reesei ALKO2466 (Suominen et al., 1993). 3'-fragment can be used together with the promoter area to target the egl2 cDNA to the cbh1 locus by homologous recombination.

amdS gene: The gene has been isolated from Aspergillus nidulans and it is coding for acetamidase (Hynes et al., 1983). Acetamide enables the strain to grow by using acetamide as the only nitrogen source and this characteristics has been used from selecting the transformants. The 3.1 kb SpeI-XbaI fragment from the plasmid p3SR2 (Kelly and Hynes, 1985) was used in the pALK537 plasmid.

The standard DNA methods described by Maniatis et al. (1982) were used in construction of the vectors. The restriction enzymes, T4 DNA ligase, Klenow fragment of DNA polymerase I and alkaline phosphatase from calf intestine used in the DNA manipulations were from Boehringer (Germany) and New England Biolabs (USA). Each enzyme was used according to the supplier's instructions. Plasmid DNA from E. coli was isolated by using the ?Qiagen colums (Diagen GmbH, Germany) according to the supplier's instructions. DNA fragments for cloning or transformations were isolated from low melting point agarose gels (FMC Bioproducts, USA) by the freeze thaw phenol method (Benson, 1984). The oligonucleotides used in the PCR-reactions and in sequencing reactions were synthetized by a ABI (Applied Biosystems, USA). Sequencing of the fusion was carried out by the automated sequencer (Applied Biosystems 373A, USA).

T. reesei VTT-D-79125 was transformed with the 9.2 kb linear NotI fragment of pALK537 as described by Penttilä et al. (1987). T. reesei transformants were transferred on a selective medium and purified through conidia. The purified transformants were grown in shake flasks in a medium containing 4% whey, 1.5% complex nitrogen source derived from grain, 1.5% $KH_2PO_4$ and 0.5% $(NH_4)_2SO_4$, pH 5.5. Cultures were grown at 30° C. and 250 rpm for 7 days. The activity against hydroxyethylcellulose (HEC) was measured from the culture media of the transformants. In the transformant ALKO3529 the activity against HEC (3400 ECU/ml) was about 3 fold compared to the parent strain VTT-D-79125 (1200 ECU/ml). According to Southern blot analysis ALKO3529 strain has at least two tandem copies of the transformed vector fragment containing the egl2 expression cassette.

ECU: One unit of ECU activity (endo-1.4-beta-glucanase) is defined as the amount of enzyme producing one nmole of reducing sugars as glucose in one second from the substrate hydroxyethylcellulose (HEC) 1 ECU=1 nkat (Bailey and Nevalainen, 1981).

B. Construction of EGI overproducing *T. reesei* strain

Construction of *T. reesei* EGI overproducing ALKO2656 strain, where the CBHI gene has been deleted, is described in Karhunen et al. (1993).

Figure 2:
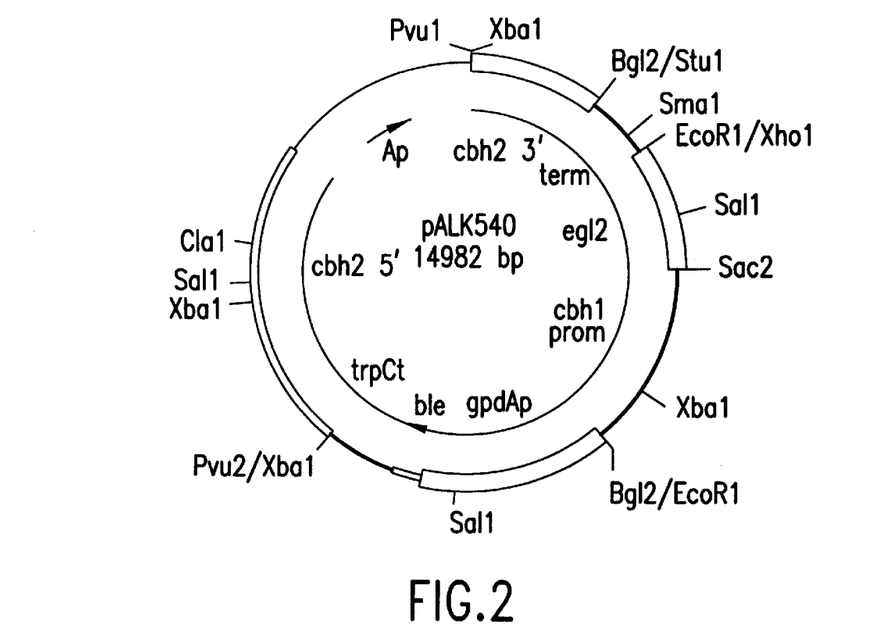
FIG. 2 shows the plasmid map of pALK540.

C. Construction of *T. reesei* strain that overproduces EGI and EGII without CBHI and CBHII For overproduction of *T. reesei* EGI and EGII without CBHI and CBHII, the expression cassette from the plasmid pALK540 (FIG. 2) was transformed to *T. reesei* ALKO2698 (Karhunen et al., 1993). ALKO2698 is an EGI overproducer that does not contain the cbh1 gene. In the cassette of pALK540 EGII is expressed from the strong cbh1 promoter. The plasmid pALK540 contains:

*T. reesei* cbh1 promoter, terminator and egl2 cDNA as described in example 1A.

ble gene. The gene has been isolated from *Streptoalloteichus hindustanus* (Drocourt et al. 1990). The gene confers resistance to bleomycin and the related antibiotics, phleomycin and tallysomycin. Resistance to phleomycin has been used for selecting the transformants. 3.3 kb XbaI-Bgl2 fragment from the plasmid pAN8-1 (Mattern et al., 1987) was used in pALK540. The fragment contains phleomycin gene (ble), flanked by the *Aspergillus nidulans* gpda promoter and trpc terminator regions.

*T. reesei* cbh2 5'-fragment. The fragment was isolated from *T. reesei* strain VTT-D-80133 (Teeri et al., 1987). A 3.4 kb XhoI-PvuII fragment starting 1.4 kb upstream from the cbh2 gene was used to target together with cbh2 3'-fragment the expression cassette to the cbh2 locus.

*T. reesei* 3'-fragment. The fragment was isolated from *T. reesei* strain VTT-D-80133 (Teeri et al., 1987). A 1.6 kb XbaI-BglII fragment starting 1.1 kb downstream from the cbh2 gene was used to target together with cbh2 5'-fragment the expression cassette to the cbh2 locus.

The same methods as described in example 1A were used in construction of the vectors.

*T. reesei* ALKO2698 was transformed with the 11.6 kb ClaI-PvuI fragment of pALK540 as described by Penttilä et al. (1987). The transformed protoplasts were plated onto surface of MnR plates osmotically stabilized with 0.44M saccharose and incubated for 6 h at 30° C., prior to the addition of 5 ml of molten MnR as an overlay containing 300 μg/ml phleomycin (Cayala, France). The transformants were purified on selective MnR-medium supplement with 50 μg/ml of phleomycin through single spore before transferring to MnR-slants containing 50 μg/ml phleomycin for three generations and after that to PD slants. The purified transformants were grown on microtiter plates for detection of the CBHII protein by Western blotting with CBHII monoclonal antibody. ALKO3528 was one of the CBHII-negative transformants and it contains one copy of the egl2 expression cassette in the place of cbh2 (Southern blot). ALKO3528 transformant was cultivated as in example 1A for measuring the activity against HEC (ECU/ml) from the culture medium. The activity against HEC was increased about 2 fold in ALKO3528 strain compared to the parent strain ALKO2698 and by 4 fold compared to the VTT-D-79125 strain which is a parent strain of ALKO2698.

D. Construction of CBHI overproducing *T. reesei* strain

Construction of *T. reesei* CBHI overproducing ALKO3760 strain is described in the International Patent Application Publication WO 96/34945.

E. Construction of CBHII overproducing *T. reesei* strain

For overproduction of *T. reesei* CBHII expression cassette from the plasmid pALK546 (FIG. 3) was transformed to *T. reesei* ALKO2221 (VTT-D-79125 mutant strain possessing a low level of protease activity). In the cassette of pALK546 CEHII is expressed from the strong cbh1 promoter.

Figure 3:
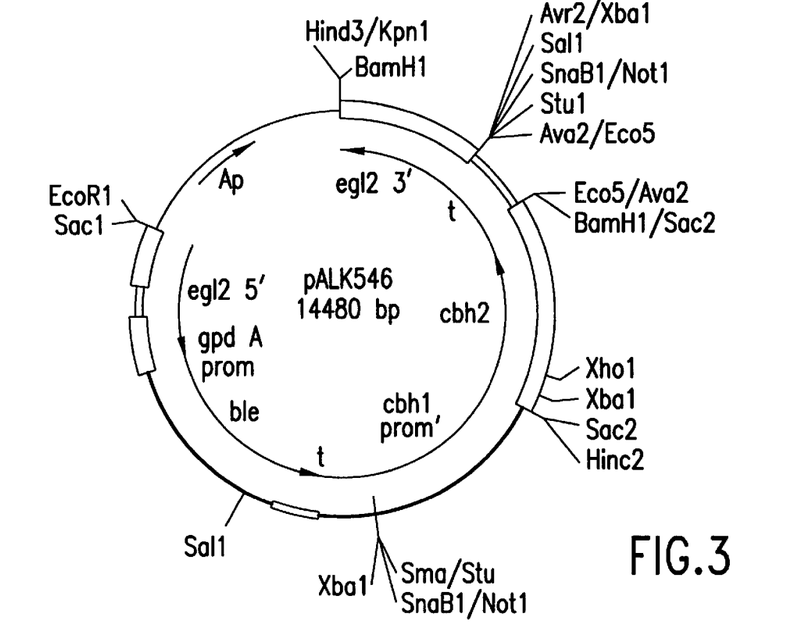
FIG. 3 shows the plasmid map of pALK546.

The plasmid pALK546 contains:

*T. reesei* cbh1 promoter and terminator as described in example 1A.

cbh2 gene. The cbh2 gene was from *T. reesei* VTT-D-80133 (Teeri et al., 1987). The fragment containing the cbh2 gene is about 2.2 kb in length, 1.5 kb of which is coding area.

ble gene, gpda promoter and trpC terminator as described in example 1C.

egl2 5'-fragment was isolated from *T. reesei* strain VTT-D-79125 and it is subcloned from a λ clone, originally called egl3, isolated by Saloheimo et al. (1988). pALK546 contains the 1.4 kb XhoI-SacI fragment about 2.2 kb upstream from the egl2 gene. This fragment can be used together with the egl2 3'-fragment to target the expression cassette to the egl2 locus.

egl2 3'-fragment. The 1.6 kb AvrII-SmaI fragment about 0.2 kb from the end of the egl2 gene was used in pALK546. The fragment originates from the same clone as the 5'-fragment.

pALK546 was constructed according to examples 1A and 1C.

*T. reesei* ALKO2221 was transformed with the 11.8 kb EcoRI-BamHI fragment of pALK546 accordingly to example 1C. The purified transformants were cultivated as in example 1A and the amount of secreted CBHII cellulase was quantitated by ELISA method (Buehler, 1991) with CBHII monoclonal antibody. In the transformant ALKO3798 the amount of CBHII protein was increased 4 fold compared to the parental strain ALKO2221. According to Southern blot analysis ALKO3798 contains one copy of the cbh2 expression cassette.

F. Construction of *T. reesei* strain that overproduces CBHI and CBHII without EGI and EGII For overproduction of *T. reesei* CBHI and CBHII without EGI and EGII expression cassette from the plasmid pALK543 (FIG. 4) was transformed to the egl2 locus of *T. reesei* ALKO3761. ALKO3761 is a CBHI overproducing EGI-negative strain. Construction of the ALKO3761 strain is described in the International Patent Publication WO 96/34945 except that the EGI-negative transformants were screened by Western blot with EGI monoclonal antibody. ALKO3761 contains one copy of the expression cassette in the egl1 locus and the secreted amount of the CBHI cellulase rose compared to the parental strain ALKO2221. In the cassette of pALK543 cbh2 is expressed under its own promoter.

Figure 4:
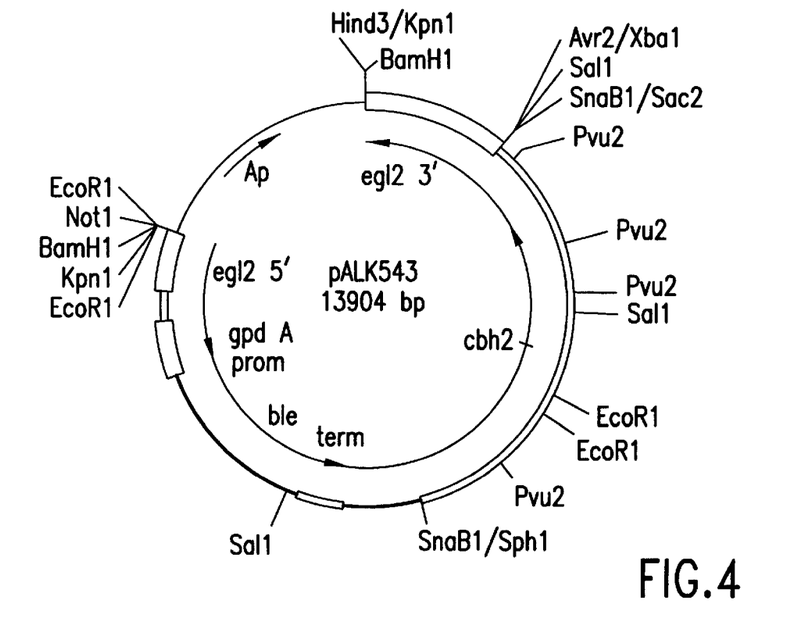
FIG. 4 shows the plasmid map of pALK543.

The plasmid pALK543 contains:

cbh2 promoter, gene and terminator from *T. reesei* VTT-D-80133 (Teeri et al., 1987). The 4.7 kb SphI-SacII fragment used in pALK543 contains approximately 1.5 kb coding area, approximately 2.5 kb promoter region and approximately 0.7 kb terminator region.

ble gene, gpda promoter and trpC terminator as described in example 1C.

egl2 5' and 3' fragments as described in example 1E.

pALK543 was constructed according to examples 1A and 1C.

*T. reesei* ALKO3761 was transformed with the 11.2 kb BamHI fragment of pALK543 and the transformants were screened accordingly to examples 1C and 1E. ALKO4097 was one of the EGII-negative transformants and according to Southern blot analysis it contains 1 copy of the cbh2 expression cassette in the egl2 locus. In ALKO4097 the amount of secreted CBHII protein was increased 3 fold compared to the parental strain ALKO3761.

EXAMPLE 2

Use of different Trichoderma cellulase preparations in biofinishing of cotton-containing woven fabric 100% cotton woven fabric (obtained from Pirkanmaan Uusi Värjäämö Ltd. Finland) was subjected to treatment with VTT-D-79125, ALKO2656, ALKO3529, ALKO3528, ALKO3760, ALKO3798, ALKO4097 cellulase preparations (example 1) in Launder-Ometer. VTT-D79125 is a hyper-cellulolytic *T. reesei* mutant strain (Nevalainen, 1985). The fabric was prewashed 10 min at 60° C. with ECOSTONE A 200 (1 ml/liter, Primalco Ltd, Biotec, Finland). 20 g of undyed prewashed fabric was used in each experiment. The cellulase treatment were performed in LP-2 Launder-Ometer (Atlas, Ill., USA) with the liquid ratio (volume of liquid per weight of fabric) of 1:15. 2 and 6 mg of total protein in cellulase preparations per g of fabric was used in each experiment. The washing time was 1 hour at pH 5, 50° C. After rinsing with alkaline and water, the treated fabrics were dried in a tumble drier (Cylinda 7703, Sweden).

The following methods were used for evaluation of the effects of the cellulase treatments on cotton fabrics: Weight loss of the treated fabrics was defined as percentage from weight of the fabric before and after the test (before weighting the fabrics were conditioning in an atmosphere of 21°+/−2° C. and 50+/−2% RH). Weight loss was used to describe the amount of fuzz removed from the fabrics surface.

Visual appearance of the enzyme treated fabrics was performed by a panel consisting of five persons. The fabrics were ranked on a score from 1 to 5, where 5 gave a clean surface with no fuzz and pills and the fabric texture became more apparent. Score of 1 gave many pills and fuzz.

The Martindale Rubbing method (SFS-4328) was used for evaluation of pilling. Pilling was evaluated on a score from 1 to 5 by a panel after 200 cycles of abrasion (1=many pills, 5=no pills). The results are shown in Table I.

TABLE I

Weight loss, visual appearance, and pilling of the fabrics treated in Launder-Ometer with different cellulase preparations

| preparation | dosage mg/g | weight loss % | visual appearance | pilling after 200 cycles |
|---|---|---|---|---|
| — | — | 0 | 1 | 1 |
| VTT-D-79125 | 2 | 0.8 | 2.3 | 2.3 |
|  | 6 | 2.2 | 2.7 | 3.6 |
| ALKO3760 | 2 | 2.1 | 3.1 | 2.3 |
|  | 6 | 4.2 | 3.4 | 3.8 |

TABLE I-continued

Weight loss, visual appearance, and pilling of the fabrics treated in Launder-Ometer with different cellulase preparations

| preparation | dosage mg/g | weight loss % | visual appearance | pilling after 200 cycles |
|---|---|---|---|---|
| ALKO3798 | 2 | 3.1 | 3.3 | 3.1 |
|  | 6 | 4.9 | 3.4 | 4.3 |
| ALKO4097 | 2 | 0 | 1.5 | 1.2 |
|  | 6 | 1.0 | 2.5 | 2.2 |
| ALKO2656 | 2 | 2.5 | 3.8 | 3.5 |
|  | 6 | 3.6 | 3.8 | 4.4 |
| ALKO3529 | 2 | 3.1 | 3.9 | 4.3 |
|  | 6 | 4.8 | 3.8 | 4.4 |
| ALKO3528 | 2 | 0.7 | 3.7 | 3.5 |
|  | 6 | 2.0 | 3.4 | 4.3 |

The results show that better visual appearance and greater ling tendency is achieved with ALKO3798 cellulase preparation than with VTT-D-79125 preparations when comparing the same dosages. The weight loss was higher with ALKO3798 treated fabrics than with VTT-D-79125 treated fabrics. This is an indication of better fuzz removal from ALKO3798 treated fabrics than from VTT-D-79125 treated fabrics.

EXAMPLE 3

Use of Trichoderma cellulase preparations in biofinishing of cotton-containing woven fabric 100% cotton woven fabric (obtained from Pirkanmaan Uusi Värjäämö Ltd, Finland) was subjected to treatment with VTT-D-79125, ALKO3760, ALKO3798, ALKO2656, ALKO3529 and ALKO3528 (example 1) preparations in Gavazzi s.r.l. Campiocolor mod. RD/1 (Italy). About 25 g undyed prewashed of fabric and 10 liter of water was used in each experiment at pH 5. The enzyme dosages were 6 and 12 mg of total protein in cellulase preparations per g of fabric. The washing times was 1 hour at pH 5 50° C.

For evaluation of the effects of the cellulase treatments on cotton fabrics the same methods were used as described in example 2. The tensile strength was measured according to the SFS standard 3981. Results are shown in Table II.

TABLE II

Weight loss, visual appearance, pilling and tensile strength of the fabrics treated in Gavazzi Campiocolor with different cellulase preparations.

| preparation | dosage mg/g | weight loss % | visual appear. | pilling after 200 cycles | tensile strength (weft) N |
|---|---|---|---|---|---|
| — | — | 0 | 1 | 1 | 15.5 |
| VTT-D-79125 | 6 | 1.9 | 2.3 | 3.2 | 14.0 |
|  | 12 | 2.6 | 2.8 | 3.6 | 13.4 |
| ALKO3760 | 6 | 2.7 | 3.6 | 3.2 | 14.2 |
|  | 12 | 3.1 | 3.1 | 3.8 | 13.4 |
| ALKO3798 | 6 | 2.8 | 3.0 | 3.5 | 13.3 |
|  | 12 | 3.9 | 3.8 | 4.5 | 12.7 |
| ALKO2656 | 6 | 2.3 | 3.1 | 3.3 | 13.8 |
|  | 12 | 2.5 | 3.6 | 3.8 | 13.8 |
| ALKO3529 | 6 | 2.9 | 4.3 | 3.7 | 12.9 |
|  | 12 | 4.1 | 4.5 | 4.4 | 13.4 |
| ALKO3528 | 6 | 1.5 | 2.9 | 2.2 | 13.1 |
|  | 12 | 2.2 | 2.9 | 2.9 | 13.9 |

Better visual appearance and greater reduction in pilling tendency was achieved with ALKO3798 cellulase preparation than with VTT-D-79125 cellulase preparation.

EXAMPLE 4

Use of different Trichoderma cellulase preparations in biofinishing of cotton-containing knit 100% cotton knit (obtained from Apropos Finland Ltd, Finland) was subjected to treatment with VTT-D-79125, ALKO2656, ALKO3529, ALKO3528, ALKO3760 and ALKO3798 cellulase preparations (example 1) in Gavazzi s.r.1. Campiocolor mod. RD/1 (Italy). About 230 g of knit and 10 liter of water was used in each experiment at pH 5. The enzyme dosage was 6 mg of total protein in cellulase preparations per g of fabric. The washing times was 1 hour at 50° C.

For evaluation of the effects of the cellulase treatments on cotton knits the same methods were used as described in example 2

Results are shown in Table III.

TABLE III

Weight loss, visual appearance and pilling of the cotton knits treated in Gavazzi Campiocolor with different cellulase preparations.

| preparation | weight loss % | visual appearance | pilling after 200 cycles |
|---|---|---|---|
| — | 2.7 | 1 | 1.1 |
| VTT-D-79125 | 4.2 | 3.4 | 2.3 |
| ALKO3760 | 4.6 | 2.6 | 2.5 |
| ALKO3798 | 5.2 | 3.4 | 3.1 |
| ALKO2656 | 4.6 | 3.6 | 2.8 |
| ALKO3529 | 5.7 | 3.8 | 3.5 |
| ALKO3528 | 3.6 | 2.9 | 2.6 |

ALKO3798 treated knits show greater weight loss than VTT-D-79125 treated knits, which is an indication of better removal of fuzz from the fabrics surface. Better pilling removal was also obtained on ALKO3798 treated knits than on VTT-D-79125 treated knits.

References referred to in the general description and the examples are listed in the following:

REFERENCES:

Bailey, M. and Nevalainen, H. 1981. Induction, isolation and testing of stable *Trichoderma reesei* mutants with improved production of solubilizing cellulase. Enz.Micr.Tech. 3:153–157.

Benson, S. A. 1984. Bio/Techniques 2:66–68.

Bhat, K. M., McCrae, S. I. and Wood, T. M. 1989. The endo-1-4-bet-a-d-glucanase system of penicillium, aspergillus-pinophilum cellulase isolation purification and characterization of five major endoglucanase components. Carbohydrate Research 190:279–297.

Bhikhabhai, R., Johansson, G. and Pettersson, G. 1984. Isolation of Cellulolytic Enzymes from *Trichoderma reesei* QM9414. Journal of Applied Biochemistry 6:335–345.

Buehler, R. 1991. Double-antibody sandwich enzyme-linked immunosorbent assay for quantitation of endoglucanase I of *Trichoderma reesei*. Appl.Environ.Microbiol. 57:3317–3321.

Drocourt, D., Calmels, T., Reynes, J. P., Baron, M. and Tiraby, G. 1990. Cassettes of the *Streptoalloteichus hindustanus* ble gene for transformation of lower and higher eukaryotes to phleomycin resistance. Nuc. Acids Res. 18:4009.

IUPAC Commission on Biotechnology. 1984. Measurement of Cellulase Activities, Ghose, T. K.

Hynes, M., Corrick, C. and King, S. 1983. Isolation of genomic clones containing the amdS gene of *Aspergillus nidulans* and their use in the analysis of the structural and regulatory mutations. Mo.Cell.Biol. 3:1430–1439.

Karhunen, T., Mäntylä, A., Nevalainen, H. and Suominen, P. 1993. High frequency one-step gene replacement in *Trichoderma reesei*. I. Endoglucanase I overproduction. Mol.Gen.Genet. 241:515–522.

Kelly, J. and Hynes, M. 1985. Transformation of *Aspergillus niger* by the amdS gene of *Aspergillus nidulans*. EMBO J. 4: 475–479.

Lowry, O. H., Rosebrough, N. J., Farr, A. L. and Randall, R. J. 1951. Protein measurement with. the Folin phenol reagent. J. Biol. Chem. 193:265–275.

Mach, R. L., Schindler, M. and Kubicek, C. P. 1994. Transformation of *Trichoderma reesei* based on hygromycin B resistance using homologous expression signals. Curr. Genet. 25:567–570. Maniatis, T., Fritsch, E. F. and Sambrook, J. 1982. Molecular cloning: A laboratory manual. Cold Spring Harbor Laboratory, Cold Spring Harbor, N.Y., USA.

Mattern, J. E., Punt, P. J. and van den Hondel, C. A. M. J. 1988. A vector of Aspergillus transformation conferring phleomycin resistance. Fungal Genet.Newslett. 35:25.

International Patent Publication No. WO 96/34945.

Nevalainen, Genetic improvement of enzyme production in industrially important fungal strains. 1985 VTT, Technical Research Centre of Finland, publications 26, Espoo Finland.

Penttilä et al. 1987. A versatile transformation system for the cellulolytic filamentous fungus *Trichoderma reesei*. Gene 61:155–164.

Penttilä, M., Lehtovaara, P., Nevalainen, H., Bhikhabhai, R. and Knowles, J. 1986. Homology between cellulase genes of *Trichoderma reesei*: complete nucleotide sequence of the endoglucanase I gene. Gene 45:253–263.

Saloheimo, M., Lehtovaara, P., Penttilä, M., Teeri, T., Stahlberg, J., Johansson, G., Claeyssens, M., Tomme, P. and Knowles, J. 1988. EGIII, a new endoglucanase from *Trichoderma reesei*: the characterization of both gene and enzyme. Gene 63:11–21.

Schulein, M. 1988. Cellulases of *Trichoderma reesei*. Methods in Enzymology 160:234–242.

Shoemaker, S., Schweikart, V., Ladner, M., Gelfand, D., Kwok, S., Myambo, K. and Innis, M. 1983. Molecular cloning of exocellobiohydrolase from *Trichoderma reesei* strain L27. Bio/Technology 1. 691–696.

Suominen, P., Mäntylä, A., Karhunen, T., Hakola, S. and Nevalainen, H. 1993. High frequency one-step gene replacement in *Trichoderma reesei*. II Effects of deletions of individual cellulase genes. Mol.Gen.Genet. 241:523–530.

Teeri, T., Salovuori, I. and Knowles, J. 1983. The molecular cloning of the major cellulase gene from *Trichoderma reesei*. Bio/Technology 1:696–699.

Teeri, T., Lehtovaara, P., Kauppinen, S., Salovuori, I. and Knowles, J. 1987. Homologous domains in *Trichoderma reesei* cellulolytic enzymes: gene sequence and expression of cellobiohydrolase II.

van Tilbeurgh, H., Loontiens, F. G., De Bruyne, C. K. and Clayessens, M. 1988. Fluorogenic and chromogenic glycosides as substrates and ligands of carbohydrases. Methods in Enzymology 160:45–59.

Wood, T. M., McCrae, S. I., Wilson, C. A., Ehat, K. M. and Gow, L. A. 1988. Aerobic and anaerobic fungal cellulases, with special reference to their mode of attack on crystalline cellulose. FEMS Symposium No. 43, Biochemistry and Genetics of Cellulose Degradation, pp. 31–52.

What we claim:

1. A method for biofinishing cellulose containing textile material, said method comprising:
   (i) adding CBHII type components to a composition to produce a biofinishing medium; and
   (ii) biofinishing said material by treating said material with said biofinishing medium.

2. The method of claim 1, wherein said composition is a natural complete cellulase composition obtained from the fermentation medium of a microbe.

3. The method of claim 1 or 2, wherein 20–100 weight percent of the total cellulase content of said biofinishing medium is CBHII type components.

4. The method of claim 3, wherein 25–60 weight percent of the total cellulase content of said biofinishing medium is CBHII type components.

5. The method of claim 4, wherein 30–40 weight percent of the total cellulase content of said biofinishing medium is CBHII type components.

6. The method of claim 1, wherein said biofinishing medium is essentially free of CBH type components except CBHII.

7. The method of claim 1, wherein said biofinishing medium is essentially free of at least one EG type component.

8. The method of claim 1, wherein said biofinishing medium is essentially free of at least one EG type component and at least one CBH type component other than CBHII.

9. A method for biofinishing cellulose containing textile materials, said method comprising treating said materials with a biofinishing medium which comprises a cellulase composition, wherein said cellulase composition is produced by a microbe that has been modified so that said cellulase composition contains an increased weight percent of CBHII type components as compared to the weight percent of CBHII components in the cellulase composition produced by said microbe prior to said modification.

10. The method of claim 9, wherein 20–100 weight percent of the total cellulase content of said composition is CBHII type components.

11. The method of claim 10, wherein 25–60 weight percent of the total cellulase content of said composition is CBHII type components.

12. The method of claim 11, wherein 30–40 weight percent of the total cellulase content of said composition is CBHII type components.

13. The method of claim 9, wherein said cellulase composition is essentially free of CBH type components except CBHII.

14. The method of claim 9, herein said cellulase composition is essentially free of at least one EG type component.

15. The method of claim 9, wherein said cellulase composition is essentially free of at least one CBH type component except CBHII and at least one EG type component.

16. The method of claim 2 or 9, wherein said microbe is selected from the group consisting of fungi or bacteria.

17. The method of claim 16, wherein said fungi are selected from the group consisting of Trichoderma, Penicillium, Aspergillus, Humicola or Fusarium genera.

18. The method of claim 17, wherein said fungi are Trichoderma species.

19. The method of claim 18, wherein said Trichoderma is *Trichoderma reesei.*

20. The method of claim 9, wherein said modified microbe is a CBHII overproducing *Trichoderma reesei* strain.

21. The method of claim 1 or 9, wherein said biofinishing medium contains surfactants, polymers, buffers, bulking agents, preservatives, stabilizers and/or abrasion agents.

22. The method of claim 1 or 9, wherein said cellulose-containing textile material is cotton.

23. The method of claim 1 or 9, wherein the proportion of cellulosic fiber in said textile material is at least 50 percent.

24. The method of claim 1 or 9, wherein the proportion of cellulosic fiber in said textile material is at least 30 percent.

25. The method of claim 1 or 9, wherein the cellulosic fiber in the cellulose-containing textile material is selected from a group consisting of cotton, flax, ramie, jute, viscose, modified viscose fibers, lyocell and cupro.

* * * * *